United States Patent [19]
de Castro et al.

[11] 4,306,956
[45] Dec. 22, 1981

[54] DISCONTINUOUS GEL ELECTROPHORESIS PROCESS

[75] Inventors: Aurora F. de Castro, Union, Mich.; Nehemias Muniz, Mishawaka, Ind.

[73] Assignee: Miles Laboratories, Inc., Elkhart, Ind.

[21] Appl. No.: 205,668

[22] Filed: Nov. 10, 1980

[51] Int. Cl.³ ............................................ G01N 27/26
[52] U.S. Cl. ............................ 204/180 G; 204/299 R
[58] Field of Search ........... 204/180 G, 180 S, 180 R, 204/299 R; 23/230 B; 424/12

[56] References Cited

U.S. PATENT DOCUMENTS

| | | | |
|---|---|---|---|
| 3,620,947 | 11/1971 | Allen et al. | 204/180 G |
| 3,873,433 | 3/1975 | Seidel et al. | 204/180 G |
| 4,139,440 | 2/1979 | Chrambach et al. | 204/180 G |
| 4,200,508 | 4/1980 | Hirai | 204/180 G |
| 4,209,373 | 6/1980 | Bluestein et al. | 204/180 G |

*Primary Examiner*—Arthur C. Prescott
*Attorney, Agent, or Firm*—James D. McNeil

[57] ABSTRACT

An improved discontinuous sodium dodecyl sulfate polyacrylamide electrophoresis process for measuring the migration of a macromolecule through the gel is disclosed. The improvement involves the use of thymol blue, phenol red, o-cresol red, orange G, m-cresol purple and mixtures, as a tracking dye.

7 Claims, No Drawings

DISCONTINUOUS GEL ELECTROPHORESIS PROCESS

BACKGROUND OF THE INVENTION

Electrophoresis in gels is a well-known procedure for determining the molecular weight of substances such as proteins, amino acids, nucleic acids, peptides and other macromolecules by applying an external electrical potential to a gel containing unresolved macromolecules in an electrophoresis cell and measuring the relative movements of the macromolecules. The molecular weight of a molecular specie can be calculated from a set of standards after obtaining a "Ferguson" plot to establish that the charge density of the unknown substance does not deviate from that exhibited by the standards.

The use of polyacrylamide gel electrophoresis (PAGE) allowed a separation effect based on a sieving effect imparted by control of the gel pore size in a "separating gel" layer, in addition to the separation obtained by electrophoretic mobility. However, molecular weight determination by PAGE was complicated by the wide range of electrophoretic charges possessed by the macromolecules present in the system. It was then discovered that these charge differences could be negated by the addition of sodium dodecyl sulfate (SDS) to the system. Large numbers of SDS molecules associate with each protein or macromolecule; the charge of the SDS molecules imparted to the SDS-macromolecule complex is so large that differences in charge, due to the composition of the macromolecule, are not detectable.

A particularly useful electrophoresis procedure is discontinuous SDS-PAGE developed in 1964 (U.S. Pat. No. 3,384,564). Discontinuous SDS-PAGE involves the use of a multi-phase (discontinuous) buffer system, varying in chemical composition, i.e., a systematic use of pH and buffer discontinuities.

Often in discontinuous SDS-PAGE, two separately polymerized layers of polyacrylamide, designated as a "stacking gel" and a "separating gel", are prepared. The stacking gel contains a low polymer concentration and has a relatively large pore size. The large pore size allows the sample to concentrate into tightly packed zones. The separating gel contains higher polymer concentrations and has a relatively small pore size. The polymer is the result of reaction between monomer and co-monomer or cross-linking agent. The effective pore size of the polymer is an inverse function of "total monomer concentration", percent T, defined as the sum of the concentrations of acrylamide and cross-linking agent. The small pore size provides a restrictive effect and produces resolution of the sample.

The uniqueness of this kind of discontinuous SDS-PAGE consists of its ability to concentrate the sample into a narrow starting zone necessary for good resolution. This is achieved in the stacking gel which differs in ionic composition and pH from the buffers in the electrode vessels.

Concentration of the sample into a narrow starting zone produces good resolution and occurs as an interface develops when the leading ion from the buffer of the stacking gel migrates out while the trailing ion of the electrolyte buffer replaces it, both moving in the same direction. The leading ion is chosen to have a higher effective mobility than the ionic species of the sample, and therefore migrates in front of all other ions. Behind the leading ion other zones form and concentrate. The concentrated macromolecule in the samples appear to the eye as one thin "stack". The concentrated sample "stack" continues to migrate through the stacking gel with no change in characteristics until it encounters a discontinuity in entering the separating gel, either in the nature of the supporting medium, i.e., pore size, or in the buffer, e.g., pH. This change produces the separation of the different macromolecular species into discrete bands. The overall procedure in discontinuous SDS-PAGE thus involves three stages: (a) stacking; (b) unstacking; and (c) resolution.

In practice, the gels are placed in a chamber containing buffer solutions, and the sample along with a tracking dye, is placed on top of the stacking gel and under the upper electrolyte buffer. After an electrical potential is applied, the sample is electrophoresed until the tracking dye migrates within a few mm from the bottom of the gel. The separated macromolecular bands are then stained for visualization. The tracking dye is used for the measurement of the relative mobility of these bands.

The true front is the boundary, which is the point of inflection of pH, between the leading and trailing ions. The point of inflection can be detected visually (as with the tracking dye), chemically, spectrometrically (refractive index) or by radioactive label. In the systems described herein, the leading ion of the buffer system is chloride ion. The point of inflection of a chloride-containing buffer system can be determined by precipitating and fixing the chloride ions with $AgNO_3$. A more convenient method of measuring the true front comprises mixing an appropriate tracking dye with the sample to allow easy visual determination.

The tracking dye serves as the reference point for the measurement of the $R_f$ of the bands. The $R_f$ is defined as the distance that each band component has traveled from the top of the separating gel to the center of the band, divided by the distance that the leading front (tracking dye) has traveled. "Ferguson" plots of the log of $R_f$ versus the percent T (total monomer concentration of the separating gel) should be obtained to check for systematic errors. The molecular weight can be calculated by plotting a function of $R_f$ versus a function of molecular weight. While the $R_f$ values are often used for calculating the molecular weight of a macromolecular species, the $R_f$ values can be used in other ways, e.g., for determining the approximate comparative sizes of macromolecular species.

In a discontinuous SDS-PAGE system, the buffer and gel can be carefully controlled and reproduced. One of the major sources of error arises in measuring the $R_f$. In order to provide the required accuracy and precision, the migration distances of the macromolecules must be accurate, and in a system containing a tracking dye this measurement depends upon the characteristics of the tracking dye. The tracking dye must migrate with the true front, i.e., at the interface of the leading and trailing ions. The present invention provides an improvement in tracking dyes suitable for use in discontinuous SDS-PAGE.

DESCRIPTION OF THE PRIOR ART

Tracking dyes commonly used in SDS-PAGE migrate with the true front over a narrow range of concentrations. For example, as indicated in *Analytical Biochemistry*, 78 459–482 (1977), bromophenol blue under certain conditions migrates with the true front at gel concentrations of 12 to 16 percent T (defined hereinbefore). At concentrations lower than 12 percent T, the dye migrates at the trailing edge of the stack instead of the leading edge (the true front) and is unsuitable. At concentrations greater than about 16 percent T, the dye does not form a sharp band at the true front, but instead diffuses (unstacks). The same article indicates that the dye pyronin Y-SDS complex migrates with the true front at gel concentrations of 3 to 11 or 12 percent T, but the dye unstacks at gel concentrations higher than 12 percent T. A mixture of bromophenol blue and pyronin Y can be used at a gel concentration from about 3 percent to 16 percent T.

In *Methods of Protein Separation*, chapter 2, p. 89 (1976) the authors suggest bromophenol red, methyl red, fluorescein, thionin and pyronin Y-SDS complex of negative polarity, in addition to bromophenol blue, methyl green, brilliant green, methylene blue, toluidine blue and Bismark brown of positive polarity, for multiphasic buffer system of various compositions. None of the dyes of the present invention are discussed or suggested in this reference.

A study of the relative mobilities of sulfophthalein indicator dyes by electrophoresis on paper indicated that bromophenol blue has a greater mobility than cresol red, m-cresol purple and thymol blue, using phenol red as a standard. See *Inst. Khim. Realt. Osobo Chist. Khim. Veschestv*, 35, 75–79 (1973). The present inventors have observed that when these dyes are used in discontinuous SDS-PAGE systems such studies in paper are not predictive of the suitability of the dyes to mark the true front.

Both bromophenol blue, referred to above, and phenol red, a dye presently claimed for use in a SDS-PAGE system were used as tracking dyes in a non-SDS gel electrophoresis system at a gel concentration of up to 15 percent T. *Archives of Bioch. and Biophysics*, 126, 155-164 (1968). The authors did not report any advantage of use of the phenol red or bromophenol blue and did not suggest the use of phenol red in a discontinuous SDS-PAGE system.

Because of the complexity of SDS-PAGE systems, due to the effect of a possible SDS-dye interaction, the effect of the steric configuration of the dye, e.g., bulk and side groups, and possible interaction with macromolecules, it is not possible to accurately predict mobilities of different dyes in an SDS-containing system or whether or not a dye will migrate with the true front in an SDS-containing system.

The present invention employs a single tracking dye or a mixture of tracking dyes in a discontinuous SDS-PAGE electrophoresis system to allow the measurement of $R_f$ values at a wider concentration range than commonly used tracking dyes.

SUMMARY OF THE INVENTION

The present invention is directed to an improved discontinuous sodium dodecyl sulfate-polyacrylamide gel electrophoresis process for measuring the migration of a macromolecule through the gel in conjunction with the migration of a tracking dye. The improvement involves the use of thymol blue, phenol red, o-cresol red, orange G, m-cresol purple and mixtures thereof.

DESCRIPTION OF THE INVENTION

As indicated earlier, a discontinuous SDS-PAGE system often requires preparation of two separately polymerized layers of acrylamide gel, the separating gel and the stacking gel.

The separating gel was prepared by the following method. Commercially available acrylamide, in solvent-recrystallized form, or recrystallized from acetone [See *Methods of Protein Separation*, Vol. 2 (1976)] was mixed with a cross-linking agent such as N,N'-methylenebisacrylamide ("Bis") or N,N'-diallyltartardiamide ("DATD"); a free-radical catalyst activator, such as potassium persulfate, riboflavin or N,N,N',N'-tetramethylethylenediamine (TEMED); and a gel buffer solution such as chloride and tris (hydroxy methyl) aminomethane ("TRIS") to prepare a gel having a known concentration of acrylamide monomer and co-monomer. A useful range of acrylamide monomer concentration is from about ⅛ to 30 percent T; a preferred range is from about 3 to 27 percent T.

The separating gel was placed in a gel tube and allowed to solidify. After the separating gel solidified, an acrylamide stacking gel mixture was prepared and dispensed on top of the separating gel in the gel tube and allowed to polymerize. A water layer was placed over the stacking gel to provide a flat surface. The final monomer concentration of the stacking gel is not critical to the $R_f$ measurement because the $R_f$ values are calculated from the electrophoretic migration in the separating gel.

The macromolecular sample was mixed with SDS, buffer and solute, e.g., glycerol, sucrose or urea. A reducing agent, e.g., dithiothreitol or mercaptoethanol can be added. About 0.2 mM (or any amount that is visually detectable) of a thymol blue, phenol red, o-cresol red, orange G, m-cresol purple or mixtures thereof was added to the sample. Water was then added to the above mixture, and the mixture heated to about 90° to 100° C. for about 5 minutes. The heating step denatures the molecules and enables the SDS, which is an ionic detergent, to complex with the macromolecules, providing them with a large negative net charge density. The water layer on top of the gel was removed, and the sample mixture placed on the stacking gel in the gel tube.

In electrophoresis applications, as indicated earlier, a series of discontinuous buffer systems is available and commonly used. In a typical discontinuous electrophoresis procedure, a series of separating and stacking gels are prepared, with varying concentrations of buffer solution. The gel tubes are then subjected to electrophoresis at a constant current of about 2 milliamps per gel tube and the electrophoresis allowed to proceed for about 2 hours.

EXAMPLE 1

(A) Preparation of Separating Gel

A series of solutions, having the proportions shown in Table 1, was prepared by mixing together a buffer solution of 1.5 M tris(hydroxymethyl)aminomethane chloride buffer containing 0.026 M N,N,N',N'-tetramethylethylenediamine at a pH of 8.9; an aqueous solution of acrylamide and N,N'-methylenebisacrylamide (Bis); ammonium persulfate and water. The acrylamide-Bis mixture was prepared by adding 38.9 g acrylamide to 1.1 g Bis, in 100 ml water; the catalyst solution was prepared by adding 140 mg in 100 ml $H_2O$. The above components were mixed together to produce a gel having from 3 percent to 27 percent T as indicated in Table 1. A 2 ml portion was dispensed into a gel tube, water layered and allowed to solidify.

(B) Preparation of Stacking Gel

The stacking gel was prepared by mixing together the above buffer solution, the catalyst solution and an aqueous solution of acrylamide and Bis in a volume ratio of 1:2:1. The acrylamide Bis solution was prepared by adding 10 gm acrylamide and 2.5 gm Bis in 100 ml of water. Use of simple volume ratios reduces a source of error in the procedure by simplifying the gel preparation.

(C) Preparation of Reaction Mixture

The reaction mixture was prepared by mixing together equal parts of a 0.02 mM solution of thymol blue in 0.064 M Tris chloride buffer; a 4 percent aqueous solution of SDS; 0.36 M dithiothreitol (DTT) and glycerol.

A 20 $\mu$l portion of the reaction mixture was mixed with 18 $\mu$l of water and a 2 $\mu$l portion of human serum added. The sample mixture was heated between 90° and 100° C. for 5 minutes. After the water layer was removed the sample mixture was placed on the stacking gel of each tube and subjected to electrophoresis at a current of 2 milliamps/gel tube, for about 2 hours. Observation of the stained separating gels indicated that the proteins in the serum sample were successfully separated.

TABLE 1

Gel Preparation Table

| % T | Parts Gel Buffer | Parts Acrylamide & Bis | Parts Ammonium per Sulfate | Parts H₂O | Parts Total |
|---|---|---|---|---|---|
| 3 | 2.0 | 0.6 | 2.7 | 2.7 | 8.0 |
| 4 | 2.0 | 0.8 | 2.6 | 2.6 | 8.0 |
| 5 | 2.0 | 1.0 | 2.5 | 2.5 | 8.0 |
| 6 | 2.0 | 1.2 | 2.4 | 2.4 | 8.0 |
| 7 | 2.0 | 1.4 | 2.3 | 2.3 | 8.0 |
| 8 | 2.0 | 1.6 | 2.2 | 2.2 | 8.0 |
| 9 | 2.0 | 1.8 | 2.1 | 2.1 | 8.0 |
| 10 | 2.0 | 2.0 | 2.0 | 2.0 | 8.0 |
| 11 | 2.0 | 2.2 | 1.9 | 1.9 | 8.0 |
| 12 | 2.0 | 2.4 | 1.8 | 1.8 | 8.0 |
| 13 | 2.0 | 2.6 | 1.7 | 1.7 | 8.0 |
| 14 | 2.0 | 2.8 | 1.6 | 1.6 | 8.0 |
| 15 | 2.0 | 3.0 | 1.5 | 1.5 | 8.0 |
| 16 | 2.0 | 3.2 | 1.4 | 1.4 | 8.0 |
| 17 | 2.0 | 3.4 | 1.3 | 1.3 | 8.0 |
| 18 | 2.0 | 3.6 | 1.2 | 1.2 | 8.0 |
| 19 | 2.0 | 3.8 | 1.1 | 1.1 | 8.0 |
| 20 | 2.0 | 4.0 | 1.0 | 1.0 | 8.0 |
| 21 | 2.0 | 4.2 | 1.0 | 0.8 | 8.0 |
| 22 | 2.0 | 4.4 | 1.0 | 0.6 | 8.0 |
| 23 | 2.0 | 4.6 | 1.0 | 0.4 | 8.0 |
| 24 | 2.0 | 4.8 | 1.0 | 0.2 | 8.0 |
| 25 | 2.0 | 5.0 | 1.0 | 0.0 | 8.0 |
| 26 | 2.0 | 5.2 | 0.5* | 0.3 | 8.0 |
| 27 | 2.0 | 5.4 | 0.5* | 0.1 | 8.0 |

*Double concentration

As described earlier, the true front is the boundary between the leading and trailing ions. In order to determine whether the dyes used in the present invention do indicate the true front, two comparative procedures were used. One procedure involved careful measurement of the refractive index by visual observation. The second procedure involved precipitation of chloride ions with AgNO₃. The gel tubes were placed into a test tube containing about 5 ml of 0.1 M AgNO₃. After several minutes, the tubes were emptied into a beaker containing 200–300 ml distilled water and the gel rinsed with distilled water several times. The boundary marks were compared with the boundary marks obtained with the thymol blue tracking dye.

The results obtained indicated that thymol blue migrated with the true front in gel concentrations from about 3 to about 20 percent T.

EXAMPLE 2

A similar procedure was carried out using phenol red, o-cresol red, m-cresol purple and orange-G as the tracking dye, and the true front determined by comparing the boundary mark obtained with these tracking dyes to the boundary marks obtained by measurement of the refractive index and precipitation with AgNO₃. The percent T range at which the dyes showed the true front is indicated in Table 2 below.

TABLE 2

| Dye | Approximate Percent T |
|---|---|
| Phenol red | 6–27 percent |
| o-cresol red | 9–25 percent |
| M-cresol purple | 8–25 percent |
| Orange G | 8–22 percent |

Electrophoresis tests using varying combinations of the dyes described in Example 1 and 2 indicated that the dyes do not interfere with each other, i.e., the range indicated for any of the dyes used above is not effected by using a combination of dyes.

Discontinuous buffer systems at any pH are now available. The National Technical Information Service (NTIS) has available a computer output of nearly 5,000 buffer systems covering the pH range 2.5 to 11.0. This approach can be used to select an optimal variation of operational pH and variation of the relative mobilities of the buffer constituents. Routine runs can then be performed with the tracking dyes of the present invention to determine the most advantageous dye or combination of dyes for use in a system involving a given buffer and gel concentration of from about ½ to 30 percent T.

The following discontinuous SDS-PAGE system was prepared, using a procedure similar to the procedure of Example 1.

EXAMPLE 3

Varying separating gels were prepared as follows. The gel buffer solution used was 0.20 M of 2-amino-2-methyl-1,3-propanediol, containing 0.026 M N,N,N',N'-tetramethylethylenediamine, at a pH of 6.8. The acrylamide-Bis mixture and ammonium persulfate were prepared as described in Example 1. The gel buffer, acrylamide-Bis mixture, persulfate and water were mixed together in the proportions shown in Table 1, to produce gels containing varying concentrations of monomer (percent T).

The procedure described in Example 1 was used to prepare the stacking gel and the reaction mixture; the reaction mixture was then subjected to electrophoresis. The percent T range at which the dyes showed the true front is indicated in Table 3 below.

TABLE 3

| Dye | Approximate Percent T |
|---|---|
| Thymol blue | 3–12 percent |
| Phenol red | 10–22 percent |
| O-cresol red | 10–18 percent |
| M-cresol purpole | 10–18 percent |

TABLE 3-continued

| Dye | Approximate Percent T |
| --- | --- |
| Orange G | 8–18 percent |

As indicated in Example 2, tests with combinations of the various dyes indicated that the dyes do not interfere with each other.

The above test results indicate that as the conditions under which the electrophoresis is conducted are changed, e.g., change of buffer system, change of pH, etc., the range of percent T values will also vary. As indicated earlier, routine runs can be performed with the tracking dyes of the present invention, in order to determine which dye is most advantageous to use under a given set of operating conditions, within a range of from about ½ to 30 percent T.

What is claimed is:

1. In a discontinuous sodium dodecyl sulfate-polyacrylamide gel electrophoresis process involving macromolecules which includes the steps of mixing the macromolecules with sodium dodecyl sulfate and a tracking dye and adding the mixture to a support medium of polyacrylamide gel containing acrylamide monomers, placing the gel support medium in contact with an ion-containing buffer solution, subjecting the macromolecules and the support medium to a differential electrical potential to produce migration of the macromolecules, buffer ions and tracking dye, and measuring the relative migration distance by the position of the tracking dye, the improvement which comprises using as the tracking dye a dye selected from the group consisting of thymol blue, phenol red, o-cresol red, orange G, m-cresol purple, and mixtures thereof.

2. A method as claimed in claim 1 wherein the concentration of acrylamide monomers present is from about ½ to 30 percent.

3. A method as claimed in claim 2 wherein when the dye is thymol blue, the concentration of acrylamide monomer present is from about 3 to 20 percent.

4. A method as claimed in claim 2 wherein when the dye is phenol red, the concentration of acrylamide monomer present is from about 6 to 27 percent.

5. A method as claimed in claim 2 wherein when the dye is a mixture of thymol blue and phenol red, the concentration of acrylamide monomer present is from about 3 to 27 percent.

6. In a discontinuous sodium dodecyl sulfate-polyacrylamide gel electrophoresis process for determining the molecular weight of a macromolecule by mixing the macromolecules with sodium dodecyl sulfate and tracking dye and adding the mixture to a support medium of polyacrylamide gel containing acrylamide monomers, placing the gel support medium in contact with an ion-containing buffer solution, subjecting the macromolecules and the support medium to a differential electricil potential to produce migration of the macromolecules, buffer ions and tracking dye, measuring the relative migration distance by the position of the tracking dye, and calculating the molecular weight of the macromolecule, the improvement which comprises using as the tracking dye a dye selected from the group consisting of thymol blue, phenol red, o-cresol red, orange G, m-cresol purple, and mixtures thereof.

7. A method as claimed in claim 6 wherein the concentration of acrylamide monomer present is from about ½ to 30 percent.

* * * * *